United States Patent [19]

Ihara et al.

[11] Patent Number: 4,900,874
[45] Date of Patent: Feb. 13, 1990

[54] METHOD FOR PRODUCING FLUORINE-CONTAINING OLEFIN

[75] Inventors: Kiyohiko Ihara; Fumihiko Yamaguchi; Shinichi Yamane, all of Osaka, Japan

[73] Assignee: Daikin Industries, Ltd., Osaka, Japan

[21] Appl. No.: 308,926

[22] Filed: Feb. 13, 1989

[30] Foreign Application Priority Data

Feb. 12, 1988 [JP] Japan ................................. 63-31551

[51] Int. Cl.$^4$ ...................... C07C 17/24; C07C 17/00; C07C 21/18
[52] U.S. Cl. ...................................... 570/142; 570/136
[58] Field of Search ......................................... 570/142

[56] References Cited

U.S. PATENT DOCUMENTS

| | | | |
|---|---|---|---|
| 3,038,947 | 6/1962 | Coyner et al. | 570/142 |
| 3,322,840 | 5/1967 | Frisch | 570/142 |
| 3,419,628 | 12/1968 | Kaufman et al. | 570/142 |
| 3,456,024 | 7/1969 | Loree | 570/142 |
| 3,843,735 | 10/1974 | Knell et al. | 570/142 |

FOREIGN PATENT DOCUMENTS 0167097 1/1986 European Pat. Off.
2141426 12/1984 United Kingdom .

OTHER PUBLICATIONS

Chemical Abstracts, vol. 99, No. 3, Jul. 18, 1983, Columbus, Ohio, U.S.A.; I. V. Stepanov et al. "Reaction of Hydroxyl and Carbonyl Compounds . . . ", p. 569, Abstract No. 21 908m.

Houben–Weyl "Methoden der Organischen . . . ", 4th Ed., vol. v/16 Alkene, Cycloalkene, Arylalkene, 1972 Georg Thieme Verlag, Stuttgart pp. 204–212, p. 205, lines 20–28.

*Primary Examiner*—J. E. Evans
*Attorney, Agent, or Firm*—Sughrue, Mion, Zinn, Macpeak & Seas

[57] ABSTRACT

A method for producing a fluorine-containing olefin represented by formula (I):

$$CH_2=CFR_f \qquad (I)$$

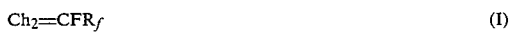

wherein $R_f$ represents a perfluoroalkyl group or a fluoroalkyl group comprising the step of contacting, at a high temperature, hydrogen gas with a 1,1-dihydro-2,2-difluoro alcohol represented by formula (II):

$$HOCH_2CF_2R_f \qquad (II)$$

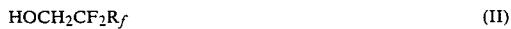

wherein $R_f$ represents a perfluoroalkyl group or a fluoroalkyl group.

9 Claims, No Drawings

METHOD FOR PRODUCING FLUORINE-CONTAINING OLEFIN

FIELD OF THE INVENTION

The present invention relates to a method for producing a fluorine-containing olefin which is useful, for example, as a monomer for modifying an ethylene/tetrafluoroethylene copolymer.

BACKGROUND OF THE INVENTION

Conventional methods for producing a fluorine-containing olefin involving a 1,1-dihydro-2-fluorovinyl group generally comprise the following steps: the hydroxyl group of a 1,1-dihydro-2,2-difluoro alcohol (referred to as a "fluoroalcohol" hereinafter) is substituted by a halogen atom; and then the resulting halide is dehalogenated with zinc.

A method for halogen substitution of a fluoroalcohol has been reported, e.g., in *J. Am. Chem. Soc.*, vol. 75, p. 5978 (1953), in which the fluoroalcohol is tosylated and then reacted with a halide such as sodium iodide. The reaction scheme is indicated below.

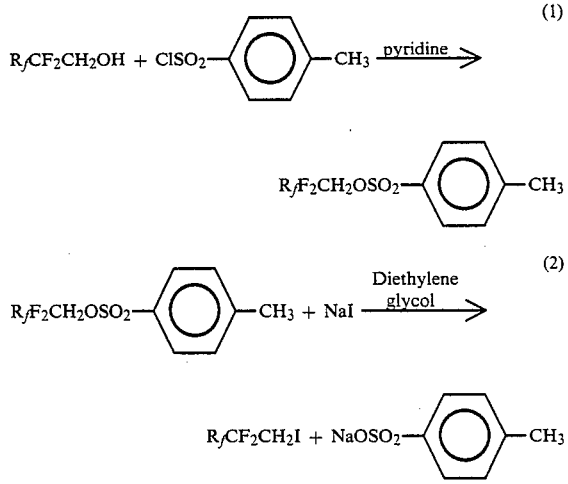

In the above formulae, $R_f$ represents a perfluoroalkyl group or a fluoroalkyl group (same as in the formulae referred hereinafter).

This method is convenient and useful in laboratory scale production, but has numerous disadvantages, such as (i) expensive reagents (such as p-toluene sulfonic acid chloride and sodium iodide) are used, (ii) in the reaction of the above formula (2), the reaction must be conducted at a high temperature using a high boiling point organic solvent (such as diethylene glycol), (iii) a large amount of waste solvents having a high boiling point must be disposed of. Therefore, this method is disadvantageous for production on an industrial scale.

Another method for halogen substitution of a fluoroalcohol has been reported, e.g., in U.S. Pat. No. 3,038,947, in which the fluoroalcohol is reacted with a thionyl halide in the presence of an amido compound as a catalyst. If the amido compound is not used, the fluoroalcohol cannot be reacted with the thionyl halide. The reaction scheme is indicated below.

$$R_fCF_2CH_2OH + SOCl_2 \xrightarrow{\text{Dimethylformamide}}$$  (3)

$$R_fCF_2CH_2Cl + SO_2 + HCl$$

This method is convenient and useful compared to the aforementioned method, but, in view of industrial production, has various disadvantages, such as the use of a toxic substance (such as thionyl chloride) and the generation of a large amount of an acidic gas.

The dehalogenation reaction of the thus obtained halide can be conducted using zinc. The reaction scheme is indicated below.

$$R_fCF_2CH_2I + Zn \rightarrow R_fCF=CH_2 + ZnIF$$  (4)

$$R_fCF_2CH_2Cl + Zn \rightarrow R_fCF=CH_2 + ZnClF$$  (5)

This reaction is relatively easy, but, in view of the industrial production, has various disadvantages, such as (i) the reaction rate is extremely low when a chloride is used, (ii) an organic solvent such as methanol or dimethylformamide is generally used in the reaction, and the waste organic solvent must be disposed of, and (iii) waste of zinc halide containing non-reacted zinc must be disposed of.

As described above, conventional methods for producing a fluorine-containing olefin have numerous disadvantages when they are practiced industrially.

SUMMARY OF THE INVENTION

An object of the present invention is to provide a method for producing a fluorine-containing olefin involving a 1,1-dihydro-2-fluorovinyl group which is free from the above prior art problems, can easily be practiced industrially, produces less amounts of waste, and can be conducted cheaply.

Other objects and effects of the present invention will be apparent from the following description.

The present inventors have conducted various investigation for attaining the above objects of the present invention, and have found that a fluorine-containing olefin involving a 1,1-dihydro-2-fluorovinyl group is produced when a fluoroalcohol is contacted with hydrogen gas. The present invention was achieved based on this finding.

The present invention therefore relates to a method for producing a fluorine-containing olefin represented by formula (I):

$$CH_2=CFR_f$$  (I)

wherein $R_f$ represents a perfluoroalkyl group or a fluoroalkyl group comprising the step of contacting, at a high temperature, hydrogen gas with a 1,1-dihydro-2,2-difluoro alcohol represented by formula (II):

$$HOCH_2CF_2R_f$$  (II)

wherein $R_f$ represents a perfluoroalkyl group or a fluoroalkyl group.

DETAILED DESCRIPTION OF THE INVENTION

The term "perfluoroalkyl group" as used herein means an alkyl group in which all the hydrogen atoms have been substituted by fluorine atoms. The term "fluoroalkyl group" as used herein means an alkyl group in which a part of the hydrogen atoms have been substituted by fluorine atoms.

By the method according to the present invention, a fluorine-containing olefin involving a 1,1-dihydro-2-fluorovinyl group can be produced cheaply by a simple procedure, i.e., a single-step reaction, with less amounts of waste.

As a preferred embodiment of the method according to the present invention, a method in which a mixture of a fluoroalcohol and hydrogen gas is passed in a gaseous state through a reaction tube which is maintained at a high temperature is practically preferred. The reaction tube used in this embodiment is not limited in form, material, etc., and may be a conventional tubular reaction tube in which the interior of the tube can be maintaind at a desired temperature by heating from the outside, as described e.g., in JP-B-47-26484 and JP-A-60-185734. (The term "JP-B" as used herein means an "examined Japanese patent publication", and the term "JP-A" as used herein means an "unexamined published Japanese patent application") The material for forming the reaction tube may be stainless steel in case of the use for a relatively short period, but is preferably Hastelloy, Inconel, etc., which are excellent in corrosion resistance.

A filler filled in the reaction tube may be used in the present invention. Examples of the filler include activated carbon, silica gel, alumina, zinc oxide, acid clay and potassium fluoride. The filler is preferably activated carbon in view of the selectivity of the objective product to by-products, e.g., $HCF_2R_f$, $CH_3CF_2R_f$ and $CH_2=CF_2$. The activated carbon may be activated with zinc chloride or the like The activated carbon which can be used as the filler is described specifically, e.g., in *Genso-betsu Shokubai Binran* (Shokubai Kagaku Koza Vol. 10) (Manual of Catalysts by Elements (Lectures on Catalysts Vol. 10)), published on 1967 (Chijin Shokan, Japan).

When the molar ratio of hydrogen gas to the fluoroalcohol is increased, the selectivity of the final product tends to increase. If the ratio of hydrogen gas is too small, the amount of the decomposition products of the fluoroalcohol increases. Thus, the molar ratio of hydrogen gas to the fluoroalcohol is preferably 1 or more, more preferably from 2 to 7, and most preferably from 3 to 5.

The reaction temperature of the present invention is preferably from 350° to 700° C., and more preferably from 400° to 650° C. If the reaction temperature is too low, the reaction cannot sufficiently proceed. If the reaction temperature is too high, undesirable decomposition reactions tend to occur.

The fluoroalcohol used in the present inventoin is a 1,1-dihydro-2,2-difluoro alcohol that has a vapor pressure at the above reaction temperature represented by formula (II):

$HOCH_2CF_2R_f$     (II)

wherein $R_f$ represents a perfluoroalkyl group or a fluoroalkyl group. Examples of the 1,1-dihydro-2,2-difluoro alcohol include the fluoroalcohol represented by formula (IIa):

$XC_nF_{2n}CH_2OH$     (IIa)

wherein X represents a hydrogen atom or a fluorine atom and n represents an integer of from 2 to 12, and preferably X represents a hydrogen atom and n represents 1, 3 or 5.

Therefore, examples of the fluorine-containing olefin involving a 1,1-dihydro-2-fluorovinyl group corresponding the above examples of fluoroalcohols include a compound represented by formula (Ia):

$XC_{n-1}F_{2(n-1)}CF=CH_2$     (Ia)

wherein X represents a hydrogen atom or a fluorine atom, and n represents an integer of from 2 to 12.

The reaction scheme of the present invention is indicated below.

$$R_fCF_2CH_2OH + H_2 \xrightarrow{(Heat)} R_fCF=CH_2 + HF + H_2O$$

Other conditions such as the pressure and the contacting time of the reaction of the present invention are not particularly limited, but the pressure of the reaction pressure is generally from 0.5 to 5 kg/cm², and the contacting time of the reaction is generally from 0.1 to 120 seconds. Preferably, the reaction pressure is from 0.5 to 1.5 kg/cm², and the contacting time of the reaction is from 1 to 10 seconds.

The objective product of the present invention can be isolated by known methods such as distillation after removing hydrogen fluoride by washing with water and drying with $CaCl_2$ or Molecular Sieves (a trade name of Linde Co.).

The present invention is described in more detail by referring to the following examples but the present invention is not construed as being limited thereto.

EXAMPLE 1

A tube made of stainless steel (SUS-316) having an inner diameter of 15.25 mm and a length of 650 mm as a reaction tube was placed in a longitudinal tubular electric furnace whose temperature was controllable having a length of 600 mm so as to fabricate a reaction device.

After granular activated carbon (specific surface area: 800 to 1,200 m²/g, activated by zinc chloride) was filled in the reaction tube, the temperature of the interior of the reaction tube was maintained at 500° C. A mixed gas of 1,1,5-trihydro-2,2,3,3,4,4,5,5-octafluoropentanol ($HOCH_2CF_2CF_2CF_2CF_2H$) and hydrogen gas at a molar ratio of ⅓ was introduced into the reaction tube from the upper side such that the contacting time was 4 seconds and the reaction pressure was atmospheric pressure.

After 1 hour from the start of the reaction, gas exhausted from the lower side of the reaction tube was analyzed by a gas chromatography. As a result, 1,1,5-trihydro-2,3,3,4,4,5,5-heptafluoropentene-1 ($CH_2=CFCF_2CF_2CF_2H$) was obtained while the conversion ratio of the starting fluoroalcohol was 64% and the selectivity to the reaction product was 82%.

EXAMPLES 2 TO 5

The same procedures as in Example 1 were repeated except that the starting fluoroalcohol, the filler in the reaction tube, the reaction temperature, the molar ratio of the fluoroalcohol and hydrogen, and the contacting time were varied as shown in Table 1 below. The results obtained are shown in Table 1 with the results of Example 1.

TABLE 1

| | Reaction conditions | | | | | Results of reaction | | |
|---|---|---|---|---|---|---|---|---|
| Example | Fluoro-alcohol | Filler | Temperature (°C.) | Fluoro-alcohol/hydrogen (molar ratio) | Contacting time (Sec) | Conversion ratio (%) | Fluorine-containing olefin | Selectivity (%) |
| 1 | $H(CF_2)_4CH_2OH$ | Activated carbon | 500 | ⅓ | 4.0 | 64 | $H(CF_2)_3CF{=}CH_2$ | 82 |
| 2 | $H(CF_2)_4CH_2OH$ | Activated carbon | 600 | 1/5 | 6.7 | 59 | $H(CF_2)_3CF{=}CH_2$ | 63 |
| 3 | $H(CF_2)_4CH_2OH$ | none | 500 | ⅓ | 6.4 | 30 | $H(CF_2)_3CF{=}CH_2$ | 51 |
| 4 | $H(CF_2)_6CH_2OH$ | Activated carbon | 500 | ¼ | 4.5 | 68 | $H(CF_2)_5CF{=}CH_2$ | 60 |
| 5 | $H(CF_2)_2CH_2OH$ | none | 500 | ⅓ | 5.3 | 25 | $CF_3CF{=}CH_2$ | 70 |

It is clear from the results shown in Table 1 that a fluorine-containing olefin involving a 1,1-dihydro-2-fluorovinyl group can be produced cheaply by a simple procedure, i.e., a single-step reaction, with less amounts of waste in accordance with the present invention.

While the invention has been described in detail and with reference to specific examples thereof, it will be apparent to one skilled in the art that various changes and modifications can be made therein without departing from the spirit and scope thereof.

What is claimed is:

1. A method for producing a fluorine-containing olefin represented by formula (I):

$$CH_2{=}CFR_f \qquad (I)$$

wherein $R_f$ represents a perfluoroalkyl group or a fluoroalkyl group
    comprising the step of contacting, at a high temperature, hydrogen gas with a 1,1-dihydro-2,2-difluoro alcohol represented by formula (II):

$$HOCH_2CF_2R_f \qquad (II)$$

wherein $R_f$ represents a perfluoroalkyl group or a fluoroalkyl group.

2. A method as claimed in claim 1, comprising the step of
    passing a mixed gas comprising said 1,1-dihydro-2,2-difluoro alcohol and hydrogen gas in which the molar ratio of hydrogen gas to said 1,1-dihydro-2,2-difluoro alcohol is 1 or more
    through a reacting tube at a temperature of from 350° to 700° C.

3. A method as claimed in claim 2, wherein the molar ratio of hydrogen gas to said 1,1-dihydro-2,2-difluoro alcohol is from 2 to 7.

4. A method as claimed in claim 3, wherein the molar ratio of hydrogen gas to said 1,1-dihydro-2,2-difluoro alcohol is from 3 to 5.

5. A method as claimed in claim 2, wherein said reaction temperature is from 400° to 650° C.

6. A method as claimed in claim 2, wherein the pressure of said reaction is from 0.5 to 5 kg/cm².

7. A method as claimed in claim 6, wherein the pressure of said reaction is from 0.5 to 1.5 kg/cm².

8. A method as claimed in claim 2, wherein the contacting time of said reaction is from 0.1 to 120 seconds.

9. A method as claimed in claim 8, wherein the contacting time of said reaction is from 1 to 10 seconds.

* * * * *